United States Patent
Rugnone

(10) Patent No.: US 10,550,075 B2
(45) Date of Patent: Feb. 4, 2020

(54) PROCESS FOR INTEGRATED PRODUCTION OF UREA AND UREA-AMMONIUM NITRATE

(71) Applicant: Casale SA, Lugano (CH)

(72) Inventor: Luca Rugnone, Como (IT)

(73) Assignee: Casale SA (CH)

( * ) Notice: Subject to any disclaimer, the term of this patent is extended or adjusted under 35 U.S.C. 154(b) by 0 days.

(21) Appl. No.: 16/461,719

(22) PCT Filed: Sep. 4, 2017

(86) PCT No.: PCT/EP2017/072054
§ 371 (c)(1),
(2) Date: May 16, 2019

(87) PCT Pub. No.: WO2018/091158
PCT Pub. Date: May 24, 2018

(65) Prior Publication Data
US 2019/0359558 A1    Nov. 28, 2019

(30) Foreign Application Priority Data

Nov. 18, 2016 (EP) .................................. 16199479

(51) Int. Cl.
*C07C 273/04*     (2006.01)
*C07C 273/16*     (2006.01)
*C07C 273/10*     (2006.01)
*C05C 9/00*       (2006.01)
*B01D 3/00*       (2006.01)
*C05C 1/00*       (2006.01)
*C07C 275/02*     (2006.01)

(52) U.S. Cl.
CPC .............. *C07C 273/04* (2013.01); *B01D 3/00* (2013.01); *B01D 3/009* (2013.01); *C05C 1/00* (2013.01); *C05C 9/00* (2013.01); *C05C 9/005* (2013.01); *C07C 273/10* (2013.01); *C07C 273/16* (2013.01); *C07C 275/02* (2013.01)

(58) Field of Classification Search
CPC ... C07C 273/04; C07C 273/16; C07C 273/10; C07C 275/02; C05C 9/005; C05C 9/00; C05C 1/00; B01D 3/00; B01D 3/009
See application file for complete search history.

(56) References Cited

U.S. PATENT DOCUMENTS

2018/0071653 A1*   3/2018   Dobree .................... B01D 3/00

FOREIGN PATENT DOCUMENTS

WO         2016/153354 A1     9/2016

OTHER PUBLICATIONS

International Search Report issued in connection with PCT/EP2017/072054.

* cited by examiner

*Primary Examiner* — Jafar F Parsa
(74) *Attorney, Agent, or Firm* — Akerman LLP

(57) ABSTRACT

Integrated process for the production of urea and urea-ammonium nitrate, comprising: reacting ammonia and carbon dioxide to form a reaction mixture (4) containing urea and unconverted materials, and also comprising the recovery of unconverted materials in a first recovery stage at a first pressure and in a second recovery stage at a second pressure, wherein ammonia-containing offgas (19) released by said second recovery stage are condensed at said second pressure, and said condensed offgas (20) are recycled to said first recovery stage.

19 Claims, 7 Drawing Sheets

PROCESS FOR INTEGRATED PRODUCTION OF UREA AND UREA-AMMONIUM NITRATE

This application is a national phase of PCT/EP2017/072054, filed Sep. 4, 2017, and claims priority to EP 16199479.3, filed Nov. 18, 2016, the entire contents of both of which are hereby incorporated by reference.

DESCRIPTION

Field of the Invention

The invention relates to the field of integrated production of urea and urea-ammonium nitrate (UAN). In some embodiments of the invention the production of urea and UAN is further integrated with the production of nitric acid.

Prior Art

Urea is synthesized by reacting ammonia and carbon dioxide. An overview of the industrial synthesis of urea starting from ammonia and carbon dioxide can be found in the Ullmann's Encyclopedia of Industrial Chemistry, Wiley-VCH Verlag.

The synthesis of urea basically takes place at a high pressure (generally greater than 100 bar) and comprises the formation of ammonium carbamate and the conversion (dehydration) of said ammonium carbamate to urea and water. Due to chemical equilibria, the conversion of the reagents into urea is not complete and, consequently, the synthesis stage produces a reaction mixture which is basically an aqueous solution of urea containing a significant amount of unconverted ammonium carbamate and ammonia.

The urea synthesis processes can be differentiated according to the way said unconverted materials are dealt with.

A total-recycle urea process is a process where essentially all of the unconverted materials in the reaction mixture are recycled to the synthesis stage. A partial-recycle process is a process where only a portion of said unconverted materials are recycled, while a once-through urea process involves no recycle of said unconverted materials.

Non-recycled unconverted materials are usually removed from the mixture as offgas, in order to obtain a urea product in the form of a solution essentially consisting of water and urea. Accordingly, a partial-recycle process and a once-through process release offgas which contain ammonia and carbon dioxide, as well as a certain amount of water vapour. For example, the unconverted ammonium carbamate is decomposed to NH3 and CO2 gas by heating the reaction mixture at a low pressure and said gas is separated from the mixture.

In modern total recycle urea plants, the reaction mixture is subjected to a stripping process, possibly with a stripping medium such as gaseous carbon dioxide. Gaseous ammonia and CO2 liberated by the stripping process are condensed to form again ammonium carbamate and recycled to a high-pressure synthesis loop. The concentrated solution leaving the stripping process is then treated into one or more recovery section(s) operating at one or more lower pressure levels, for further recovery. The recovery section(s) produce a purified aqueous urea solution and a liquid carbamate solution which is recycled back to the urea synthesis.

Typically, in the total-recycle CO2-stripping urea plants the urea solution leaving the high pressure stripper is directly treated in a low pressure recovery section operating at 2-5 bar. In the total-recycle self-stripping process the urea solution is treated in a medium pressure recovery section and further treated in a low pressure recovery section.

Eventually, all the above mentioned urea processes produce an aqueous solution of urea whose concentration is typically 70-80% with minor amounts of impurities.

Said aqueous solution of urea can be further treated to remove essentially all water, obtaining a urea melt which is processed in a finishing section to produce solid urea, e.g. in the form of prills or granules.

Another use of said aqueous solution of urea is the production of UAN which is a known and widely used liquid fertilizer.

The production of UAN involves mixing the urea aqueous solution with ammonium nitrate. Ammonium nitrate is produced by reacting ammonia and nitric acid, and ammonia is also a feedstock for the production of nitric acid and for the production of urea. Accordingly, a process for the production of UAN can be advantageously integrated with the production of urea and also with the production of nitric acid.

Despite being outdated compared to the modern total-recycle processes, the once-through process and the partial-recycle process are still of interest for integration with the production of ammonium nitrate and possibly of nitric acid because the large amount of ammonia- and carbon dioxide-containing offgas can be used as source material.

Further integration can be made with a section for the synthesis of ammonia starting from a hydrocarbon feedstock such as natural gas or a methane-containing synthesis gas.

A prior art integrated process for the production of UAN, ammonium nitrate and nitric acid follows this scheme:

i) A urea synthesis stage produces an aqueous solution of urea and releases a first offgas stream at a medium pressure (MP offgas), usually in the range 8-15 bar, and a second off gas stream at a near-atmospheric pressure (e.g. 0.5 bar relative). Both offgas streams contain ammonia, carbon dioxide and some water vapour.

ii) The aqueous solution of urea is used, in full or in part, to feed a UAN stage.

iii) The MP offgas containing unconverted ammonia, carbon dioxide and water vapors feed a Nitric Acid (NA) stage, which produces an aqueous solution of nitric acid (HNO3).

iv) The atmospheric offgas which contains unconverted ammonia, carbon dioxide and water vapour, and the nitric acid solution, feed an Ammonium Nitrate (AN) stage which produces ammonium nitrate.

v) The ammonium nitrate is fed to the UAN stage where it mixes with the urea solution to form the desired urea-ammonium nitrate product.

The first offgas stream (MP offgas) originates from a medium-pressure recovery section which processes the reaction mixture from a high-pressure reactor or high-pressure synthesis loop, and produces a more concentrated aqueous solution of urea.

The reaction mixture is expanded from the high synthesis pressure to the medium pressure urea recovery, then is treated in a MP decomposer releasing ammonia and carbon dioxide by decomposition of unconverted ammonium carbamate and obtaining a concentrated urea solution at medium pressure.

The second offgas stream originates from a second recovery section which processes the above mentioned aqueous solution of urea effluent from the medium-pressure recovery section. Said second recovery section generally comprises at least a decomposer and a liquid-gas separator.

The term of decomposer denote equipment where the urea solution is heated to decompose the ammonium carbamate into urea and carbon dioxide. A typical embodiment of decomposer is a steam-heated shell-and-tube heat exchanger.

The production of ammonium nitrate in the AN stage involves the neutralization of nitric acid with ammonia in a reactor which is also termed "neutralizer".

The above described scheme of the prior art provides a good integration between the different synthesis stages. However, it has some drawbacks.

A first drawback is that the MP offgas recycled to the NA stage contain a significant amount of CO2 which is inert to the production of nitric acid and is discharged as such by the NA stage. This amount of CO2 increases the flow rate and then the size and cost of equipment, while providing no contribution to the synthesis of nitric acid.

A second drawback is that the starting materials for the synthesis of ammonium nitrate are fed to the AN stage at a very low pressure, near atmospheric. As a consequence, the neutralizer of the AN stage is forced to operate at a low pressure, i.e. slight vacuum or about atmospheric pressure.

The low pressure of the AN stage and low pressure of the offgas feed may result in a poor mixing of ammonia vapours and nitric acid and, consequently, uncomplete conversion. Uncomplete conversion is a disadvantage from the economic point of view and entails the risk of ammonia emissions into the atmosphere.

The unconverted ammonia which escapes the neutralizer is generally recovered in a scrubbing system which, however, may be overloaded especially when the production capacity is pushed to its limits. Release of ammonia into atmosphere must generally be avoided, which means that said scrubbing system may constitute a bottleneck against increase of capacity of the plant.

A third drawback is given by the safety concerns about the atmospheric neutralizer. Said neutralizer, operating at such low pressure, needs a large volume and a considerable residence time. The larger the volume and residence time, the higher the risk due to the presence of toxic, dangerous and potentially flammable and explosive materials.

The prior art teaches to feed all the available MP offgas directly to the NA stage because the pressure of said offgas (typically 8-15 bar) corresponds to the pressure of use in the NA stage. However this means that only atmospheric offgas remain available for the ammonium nitrate stage with the drawbacks described above.

Furthermore, the prior art CO2-stripping or self-stripping total recycle urea processes are stand-alone processes since all ammonia and carbon dioxide are recycled to the synthesis and they are not made available for the production of ammonium nitrate. In the prior art, when the production of UAN and/or nitric acid is desired, a nitric acid plant or ammonium nitrate plant is designed as a completely independent facility.

SUMMARY OF THE INVENTION

The invention aims to solve the above drawbacks. The invention in particular aims to a more efficient integration between the urea stage and the ammonium nitrate stage when a urea-ammonium nitrate product is produced.

The invention also aims to a better integration with a nitric acid stage if provided. The invention aims also to increase safety and reduce emissions, particularly the risk of emissions of ammonia. Furthermore, the invention aims to provide a technique for increasing the capacity of existing plants for the production of urea-ammonium nitrate and debottlenecking of said plants.

The above aims are reached with a process for the production of urea and urea-ammonium nitrate, comprising:
a) the production of aqueous solution of urea starting from ammonia and carbon dioxide,
b) the production of ammonium nitrate from ammonia and nitric acid in a ammonium nitrate stage
c) wherein at least part of said aqueous solution of urea is mixed with at least part of the ammonium nitrate to produce urea-ammonium nitrate in a urea-ammonium nitrate stage,
d) the production of said solution of urea comprising the reaction of ammonia and carbon dioxide at a synthesis pressure to form a urea reaction mixture containing urea and unconverted materials, and also comprising the recovery of unconverted materials in a plurality of recovery stages including at least a first recovery stage operating at a first recovery pressure lower than said synthesis pressure, and a second recovery stage operating at a second recovery pressure lower than said first recovery pressure, the process being characterized by:
e) offgas released by a step of carbamate decomposition in the second recovery stage are at least partially condensed at said second recovery pressure, obtaining condensate offgas;
f) recycling at least part of said condensate offgas, or a solution containing at least part of said condensate offgas, to said first recovery stage;
g) withdrawing an ammonia-containing stream from said first recovery stage at said first recovery pressure or at slightly lower pressure, and feeding said ammonia-containing stream to the ammonium nitrate stage.

In a preferred embodiment, the above process further comprises the production of aqueous nitric acid from ammonia and air. In embodiments including the production of nitric acid, the process preferably comprises: withdrawing from the first recovery stage a CO2-free stream containing at least 98% weight ammonia having the proper pressure and composition for the synthesis of the nitric acid solution.

According to different embodiments of the invention, the production of urea can take place with a total-recycle process, a partial-recycle process or a once-through process. A total recycle process can be for example a CO2-stripping or self-stripping process. The synthesis of urea is preferably carried out at a high pressure, for example 70 to 300 bar.

If urea is produced with a total recycle process, the off gas stream withdrawn from said first recovery stage are substantially free of CO2 since all the CO2 is recovered in the form of liquid ammonium carbamate in said first recovery stage and recycled back to the urea synthesis.

If urea is produced with a once-through or partial-recycle process, the offgas withdrawn from said first recovery stage contains also unconverted CO2.

The ammonia feed necessary for the UAN production is preferably injected in a single point to the urea stage. Said single injection point is preferably in the first recovery stage or directly in the high-pressure urea synthesis stage. The ammonia which exceeds the stoichiometric needs for the production of urea is withdrawn to the nitric acid plant (if provided) and ammonium nitrate plant. The ammonia feed is preferably at least 99% ammonia by weight.

In the urea stage, each recovery stage processes a solution comprising urea and unconverted materials coming from the synthesis or from a previous recovery stage at a higher pressure. A recovery stage may comprise a decomposer or a dissociator wherein the solution is heated to decompose the ammonium carbamate into ammonia and carbon dioxide, a gas/liquid separator where the effluent of the decomposer is separated into a liquid phase of urea solution and a gaseous phase containing ammonia and carbon dioxide, and a condenser.

Each recovery stage is preferably carried out in a respective recovery section.

Each recovery stage operates at a respective recovery pressure. The recovery stages form a cascade from a first and highest pressure to a lowest pressure. The first recovery stage operates at a first recovery pressure which is the highest of recovery pressures, whilst the last recovery stage operates at a pressure which is the lowest.

The pressure of the first recovery stage is preferably in the range 2 to 25 bar, preferably 5 to 20 bar and more preferably 8 to 20 bar. This pressure is also termed medium pressure and the first recovery stage is also termed a medium-pressure recovery stage.

In some embodiments the pressure of the last recovery stage is atmospheric pressure or is a near-atmospheric pressure slightly above the atmospheric pressure. Preferably said near-atmospheric pressure is not greater than 1 barg and more preferably about 0.5 barg. The symbol barg (bar gauge) denotes the pressure relative to atmospheric pressure.

In preferred embodiments of the invention the recovery stages are two or three. An embodiment of the invention includes two stages, namely a first recovery stage at 8 to 20 bar and a second recovery stage at near-atmospheric pressure. Another preferred embodiment has three recovery stages: a medium-pressure stage at 8 to 20 bar, a low-pressure stage at 2 to 6 bar, an atmospheric stage at near-atmospheric pressure.

The term of near-atmospheric pressure denotes a pressure equal to or slightly greater than the atmospheric pressure.

Each recovery stage may release offgas containing ammonia and carbon dioxide. In a preferred embodiment, the offgas withdrawn from the first recovery stage have a pressure which is equal to or substantially equal to said first recovery pressure (medium pressure).

The ammonia-containing stream withdrawn from the first recovery stage according to step g) may be an offgas stream or, in some embodiments, a liquid stream. In some embodiment this stream is a carbamate solution from the bottom of a scrubber column.

According to different embodiments, the condensate offgas obtained after said step e) can be recycled to the first recovery stage directly or through a condensation step at an intermediate third pressure.

In some embodiments the aforesaid condensate offgas, or at least a portion thereof, is used to promote condensation of vapours containing ammonia and carbon dioxide, in a third recovery stage at a pressure higher than said second pressure.

In a preferred embodiment:

the urea synthesis process comprises a third recovery stage operating at a third recovery pressure which is lower than said first recovery pressure and greater than said second recovery pressure;

said third recovery stage comprises a step of decomposition of a urea solution coming from the first recovery stage, obtaining a gas phase containing ammonia and carbon dioxide, and subsequent condensation of said gas phase;

and said step f) includes:

mixing said condensate offgas with said gas phase before or during said condensation, obtaining a carbamate solution at said third pressure, and recycling said carbamate solution to said first recovery stage.

In a preferred embodiment, said first recovery stage comprises a step of scrubbing $CO_2$ and $NH_3$ vapours with liquid ammonia and obtaining a carbamate solution. In this case the ammonia-containing stream directed to the ammonium nitrate stage may include said carbamate solution obtained after scrubbing, or may include vapours obtained from a subsequent step of decomposition of said carbamate solution. In the latter case, the vapours are offgas released from the medium-pressure recovery section.

More in detail, in a preferred embodiment, the medium-pressure recovery stage comprises: decomposition of the urea reaction mixture, obtaining a urea solution and a gas phase containing ammonia and carbon dioxide; partial condensation of said gas phase obtaining a carbamate solution; scrubbing the remaining $CO_2$ and $NH_3$ vapours after the partial condensation with liquid ammonia obtaining said carbamate solution.

Said scrubbing process takes place preferably in a scrubber column.

According to some embodiments, the above mentioned solution containing condensate offgas from the second recovery section is recycled to said scrubbing process, for use as a scrubbing means and to facilitate condensation of carbon dioxide. For example, said solution can be recycled to one or more location(s) of the scrubber column.

In a preferred embodiment said step f) includes:

recycling a first portion of said solution containing condensate offgas to said step of partial condensation of the gas phase obtained after decomposition of the reaction mixture, said first portion of solution being mixed with said gas phase before or during condensation;

recycling a second portion of said solution to said scrubbing process, for use as a scrubbing medium.

Said scrubbing step provides a distillation of vapours, recovery of a liquid carbamate solution at the bottom of the scrubber and withdrawal of a $CO_2$-free ammonia gas at the top of said scrubber.

Said carbamate solution can be recycled directly to the urea synthesis in a total-recycle process, or can be sent to a subsequent step of carbamate dissociation in a partial-recycle process.

In the above embodiments with a scrubbing process, the ammonia fed to said ammonium nitrate stage can include a stream obtained directly from said scrubbing process and/or a stream obtained from a subsequent step of decomposition of said carbamate solution (if provided).

In some embodiments, the process is further integrated with a nitric acid stage for the production of a solution of nitric acid. At least a portion of said solution of nitric acid is used for the production of ammonium nitrate in the ammonium nitrate stage and the process preferably comprises the step of: withdrawing a substantially pure ammonia gas from said first recovery stage and feeding said ammonia gas to said nitric acid stage.

Said substantially pure ammonia gas directed to the nitric acid stage can be advantageously withdrawn from the above mentioned scrubbing process.

In some embodiments, two off gas streams originate from said first recovery stage, namely a first offgas stream containing ammonia and unconverted $CO_2$ and a second offgas stream containing substantially pure ammonia.

This is the case in particular of a urea synthesis process which is not a total-recycle process. In preferred embodiments of the invention, said first offgas (also containing CO2) provides ammonia for the ammonium nitrate synthesis and the second offgas of pure ammonia feeds the nitric acid process.

According to a further preferred embodiment, said ammonia-containing stream withdrawn from the first recovery stage, either in a gaseous state or in a liquid state, is contacted with a solution of nitric acid in a pressurized pipe reactor of the ammonium nitrate stage. Preferably said pressurized pipe reactor operates at a pressure substantially equal to said first recovery pressure or slightly lower.

In preferred embodiments, said first recovery pressure is in the range 2 to 25 bar, preferably 5 to 20 bar and more preferably 8 to 20 bar, and/or said second recovery pressure is atmospheric or is a near-atmospheric pressure slightly above the atmospheric pressure, preferably being not greater than 1 barg and more preferably about 0.5 barg, and/or said third recovery pressure is 2 to 6 bar, preferably about 3 bar.

The operating pressure of the above mentioned pipe reactor is preferably 6 to 12 bar.

The ammonia-containing stream of said step g) preferably has a purity of at least 98 wt %. Said ammonia-containing stream can be liquid or gaseous (offgas).

In some embodiments the process of the invention can be further integrated with the production of melamine. A portion of the synthesized urea in this case is used to produce melamine, and melamine offgas containing ammonia and carbon dioxide are advantageously recycled to the urea synthesis process.

The main advantage of the invention is that the ammonia and carbon dioxide contained in the offgas emerging from the second recovery section at a low pressure (typically near atmospheric pressure) are condensed and recycled in a liquid form to a higher pressure, finally reaching the first recovery section. Here, the recycled ammonia and carbon dioxide contribute to the formation of offgas at a higher pressure, which can be efficiently used to feed the ammonium nitrate stage. In other words, it can be said that ammonia and carbon dioxide extracted at a low pressure from the second recovery section are condensed, pumped to a higher pressure for recycle to one or more higher-pressure recovery sections, and gasified at a higher pressure, preferably at the pressure of the first recovery stage.

On the other hand, the invention allows extraction of a current of substantially pure ammonia gas from the first recovery section, thanks to the increased ammonia recycle from lower recovery section(s), wherein said ammonia gas can feed a nitric acid stage if provided. Said pure ammonia gas is withdrawn for example from the above mentioned scrubbing process, e.g. from top of a scrubber column.

Hence the invention provides that offgas at a relatively high pressure (usually a medium pressure in the range 8-20 bar) are recycled to the ammonium nitrate section instead of the nitric acid section. The latter can be fed by the ammonia gas withdrawn from the first recovery section.

In some embodiments the offgas emerging from the first recovery section are recycled to the ammonium nitrate stage in a liquid form.

The invention overcomes the drawback of sending inert CO2 and water to the nitric acid section. The nitric acid section can be debottlenecked especially in the absorption unit where the presence of CO2 would reduce the partial pressure available for the absorption. In this way the emissions from the nitric acid section are drastically reduced.

In some embodiments, a nitric acid section can be fed with liquid ammonia produced in an ammonia section. Accordingly the nitric acid section can be decoupled from the urea section. This can be an advantage e.g. if the urea section is a bottleneck of the plant.

Feeding the ammonium nitrate section with offgas at a relatively high pressure (for example 8 to 20 bar) is a considerable advantage because the pressure energy of the feed can be used to intimately contact the ammonia-containing gas phase with the liquid phase containing HNO3 thus improving drastically the efficiency of the reaction.

In a particularly preferred embodiment, the production of ammonium nitrate is carried out in a pressurized pipe reactor. Accordingly the ammonium nitrate section comprises a pipe reactor which is fed with said medium-pressure offgas and with an aqueous solution of nitric acid. Preferably the pipe reactor operates at around 10 bar.

The pipe reactor allows intimate contact of the ammonia gas and nitric acid solution. The elevated pressure of the incoming off gas containing ammonia promotes efficient mixing between the reactants.

The outlet of the pipe reactor is preferably fed to a separator chamber at atmospheric pressure or slightly under vacuum where vapours containing mainly water as steam are separated and a hot ammonium nitrate solution is obtained, for example at 95% concentration. It shall be noted that the pipe reactor is used to react a pressurized stream of off gases containing ammonia and not only a pressurized stream of pure ammonia.

A further advantage of a pressurized pipe reactor is the lower risk of escape of unconverted gaseous ammonia thanks to the efficient mixing between ammonia and nitric acid.

Another advantage is due to the reduced volume of the pipe reactor and separator so that it is minimized the risk of release of ammonia, nitric acid and ammonium nitrate at high temperature if compared to the conventional atmospheric neutralizer of the prior art. The pressurized pipe reactor of the invention has a smaller volume and smaller residence time than said neutralizer.

An aspect of the invention is also a plant for the synthesis of urea and UAN according to the claims.

Another aspect of the invention is the modification of an existing integrated plant for urea and UAN according to the claims.

The advantages will emerge even more clearly with the aid of the description below, relating to a preferred embodiment.

DETAILED DESCRIPTION OF PREFERRED EMBODIMENTS

Figure 1:
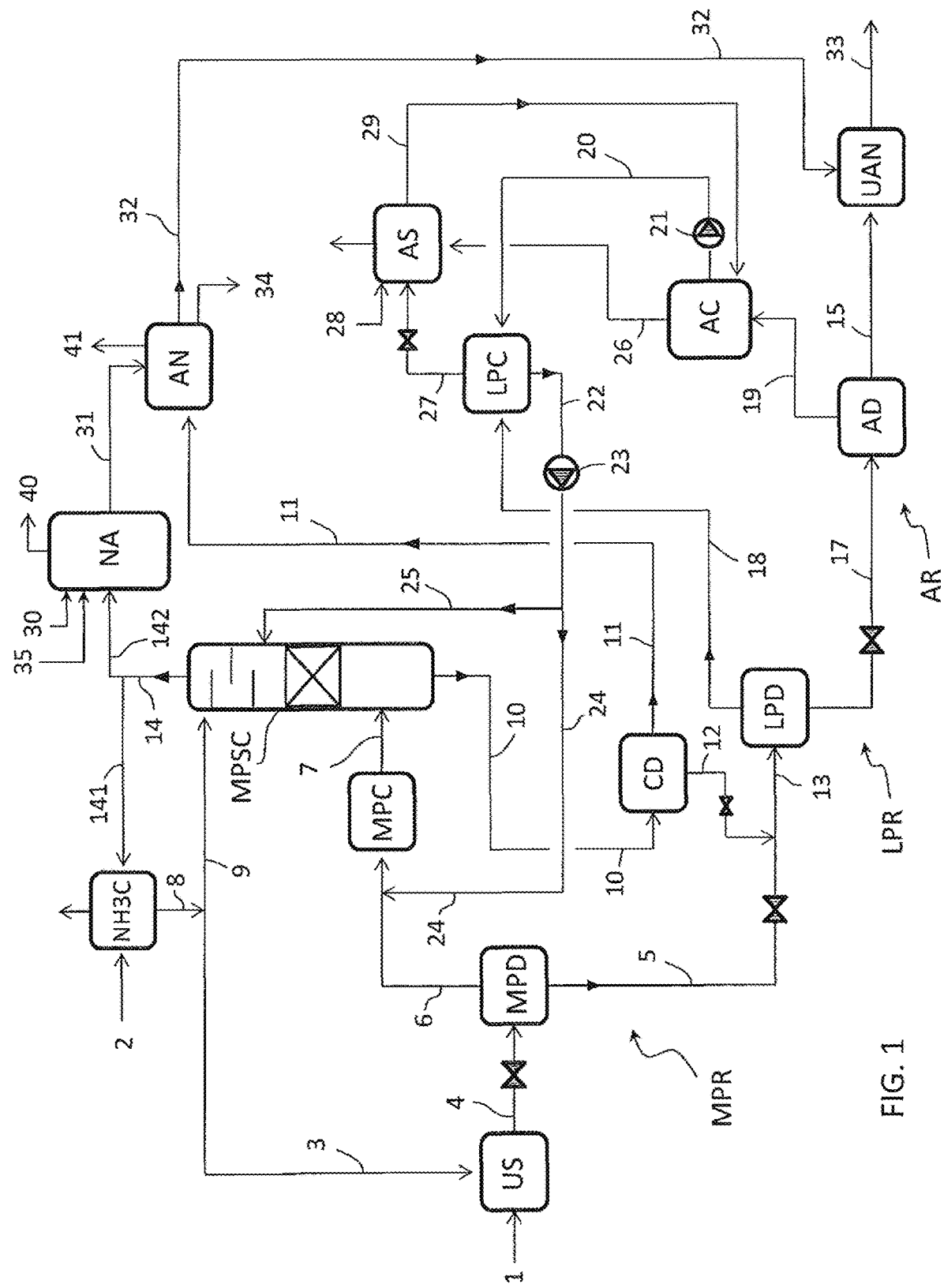
FIG. 1 illustrates an embodiment of the invention, wherein urea is produced with a partial-recycle process.

A first embodiment is described with reference to FIG. 1 wherein:

US denotes a urea synthesis section;

NA denotes section for production of nitric acid;

AN denotes a section for production of ammonium nitrate;

UAN denotes a section for production of a urea-ammonium nitrate product, by mixing urea and ammonium nitrate, MPD is a medium-pressure carbamate decomposer, MPC is a medium-pressure condenser, MPSC is a medium-pressure ammonia scrubber column, CD is a carbamate decomposer, LPD is a low-pressure carbamate decomposer, LPC is a low-pressure condenser, AD is an atmospheric carbamate decomposer, AC is an atmospheric condenser, AS is an atmospheric scrubber.

NH3C is an ammonia condenser.

MPS is a medium-pressure separator.

The medium-pressure equipment, including the decomposer MPD, the condenser MPC and the scrubber column MPSC, are part of a medium-pressure recovery section MPR.

The low-pressure equipment including the decomposer LPD and condenser LPC are part of a low-pressure recovery section LPR.

The atmospheric pressure equipment including the decomposer AD, the condenser AC and the scrubber AS, are part of a further recovery section AR.

The medium-pressure section MPR works for example at a pressure of 8 to 20 bar. The low-pressure section LPR works for example at 2 to 6 bar. The section AR works for example at just 0.5 bar above the atmospheric pressure.

The decomposers such as MPD, LPD and AD are heated for example with steam at a suitable pressure. For example said decomposers are steam-heated shell-and-tube exchangers.

An aqueous solution of urea 15 is produced starting from ammonia 3 and carbon dioxide 1, and is mixed with ammonium nitrate 32 to produce urea-ammonium nitrate 33 in the stage UAN.

The urea synthesis process of FIG. 1 comprises the reaction of ammonia 3 and carbon dioxide 1 at a synthesis pressure to form a reaction mixture 4 containing urea and unconverted materials including ammonium carbamate, carbon dioxide and ammonia.

The unconverted materials contained in the reaction mixture 4 are recovered by means of subsequent steps of decomposition of carbamate into ammonia and carbon dioxide in the decomposers MPD, LPD and AD, resulting in the aqueous urea solution 15.

Each decomposition step produces a liquid effluent (urea solution) and a gaseous phase containing ammonia and carbon dioxide. The offgas 19 released by the atmospheric decomposer AD, according to an embodiment of the invention, are condensed in the atmospheric condenser AC to form a stream of liquid condensate offgas 20. Said condensate offgas 20 is recycled to the medium-pressure recovery stage MPR, namely to the medium-pressure condenser MPC, after a passage through the low-pressure condenser LPC.

The liquid condensate offgas 20 are more diluted in water than the effluent 22 of said low-pressure condenser LPS, so that the practice of recycling the offgas 20 through the low pressure condenser LPC helps to promote the condensation of CO2 and NH3 vapours 18.

Furthermore, offgas 11 containing ammonia are withdrawn from said first recovery stage MPR, namely from the carbamate decomposer CD, and recycled to the ammonium nitrate stage AN.

FIG. 1 relates to an embodiment where production of nitric acid is further integrated with the production of urea and UAN. A substantially pure ammonia gas 14 is withdrawn from the medium-pressure recovery stage, namely from the scrubber column MPSC, and a portion 142 of said ammonia gas 14 feeds a nitric acid stage NA.

The nitric acid stage NA produces a solution of nitric acid 31 which feeds the ammonium nitrate stage AN together with the offgas 11.

The scheme of FIG. 1 is now described in a greater detail.

Fresh carbon dioxide 1 enters the urea synthesis section US, while fresh liquid ammonia 2 enters the ammonia condenser NH3C where ammonia gas 141 emerging from the column MPSC is condensed to form liquid ammonia 8.

Normally the liquid ammonia 2 is colder than the ammonia vapours 141 so that injection of said liquid ammonia 2 in the ammonia condenser NH3C helps to promote the condensation of ammonia gas 141. Part of said liquid ammonia 8 forms the ammonia input 3 directed to the urea synthesis section US. The remaining part 9 of the ammonia goes back to the column MPSC. In some embodiments the input ammonia 2 can be mixed with the ammonia stream 8 before splitting the stream 8 into the feed streams 3 and 9.

Preferably the ammonia input 2 which is fed to the ammonia condenser NH3C is the total ammonia needed by stoichiometry to make the urea-ammonium nitrate product 33. More in detail the ammonia input 2 includes the ammonia which is needed for the urea synthesis, for the nitric acid synthesis and for the neutralization of such nitric acid to produce ammonium nitrate.

The carbon dioxide 1 and ammonia 3 are reacted in the urea synthesis section US at a synthesis pressure to form the urea aqueous solution 4 (reaction mixture).

Said urea aqueous solution 4 is depressurized and sent to the medium-pressure decomposer MPD where the carbamate contained in the solution 4 is decomposed to ammonia and carbon dioxide, with the help of heat.

Said medium-pressure decomposer MPD produces a urea solution 5 which is further treated in the low-pressure recovery section LPR, and a gaseous phase 6 containing ammonia and carbon dioxide.

Said gaseous phase 6 is partially condensed in the medium-pressure condenser MPC with the help of a recycled solution 24, coming from the low-pressure recovery section LPC, which will be described later.

The partially condensate effluent 7 of the medium-pressure condenser MPC is a carbamate solution, containing also some gaseous ammonia and CO2.

Said effluent 7 is sent to the lower part of the medium-pressure ammonia scrubber column MPSC. Here the gaseous ammonia and CO2 contained in the stream 7 separate and flow upward in the scrubber MPSC. As mentioned above, said column MPSC is also fed with liquid ammonia 9. The upper part of said column MPSC further receives a recycled solution 25 from the low-pressure section LPC, which acts as a scrubbing medium of the ammonia and CO2 vapours which are contained in the carbamate solution 7.

The vapours of ammonia and CO2 contained in the effluent 7 are scrubbed in the column MPSC obtaining a carbamate solution 10 also including the liquid portion of the effluent 7. Said carbamate solution 10 is recovered from bottom of the column MPSC as a heavy component, and is sent to the carbamate decomposer CD.

The carbamate decomposer CD provides decomposition of the carbamate into ammonia and CO2 and separates the liquid and vapour phase, producing: medium-pressure offgas 11 containing ammonia (about 45%) carbon dioxide (about 40%) and water as balance to 100%, which feed the ammonium nitrate section AN, and a liquid phase 12 containing the most of the water (about 75%) and some ammonia (about 15%) and $CO_2$ (about 10%) as carbamate remaining not decomposed. Said liquid phase 12 together with the solution 5 forms the urea solution feed 13 to the low-pressure decomposer LPD.

The column MPSC removes practically all the carbon dioxide contained in the carbamate solution 7. A substantially pure CO2-free ammonia gas 14 (light component) is withdrawn from top of the column MPSC. A first part 141 of said ammonia gas 14 is sent to the ammonia condenser NH3C and another part 142 of said ammonia gas 14 feeds the nitric acid stage NA.

The decomposition of the urea solution 13 in the low-pressure decomposer LPD produces a urea solution 17 and a gaseous phase 18.

The urea solution 17 is further treated, after depressurization, in the atmospheric decomposer AD obtaining the aqueous solution of urea 15, consisting essentially of urea and water and containing 70-80% urea, and the offgas 19 containing ammonia and carbon dioxide.

The offgas 19 are at least partially condensed in the condenser AC. The so obtained condensate 20 is sent via a pump 21 to the low-pressure condenser LPC. Said pump 21 elevates the pressure of the condensate effluent of the condenser AC from the pressure of the atmospheric recovery section AR to the higher pressure of the section LPR. In the low-pressure condenser LPC, the condensate 20 promotes the condensation of the vapour phase 18 emerging from the low-pressure decomposer LPD.

The low pressure condenser LPC produces a LPR condensate solution 22 which is further elevated to the pressure of the medium-pressure recovery section MPR via a pump 23, and recycled to said section MPR.

Said LPR condensate solution 22 can be recycled to different points of the section MPR. According to a preferred embodiment, as illustrated in FIG. 1, a first portion 24 of the LPR condensate solution 22 is fed to the condenser MPC and a second portion 25 of said solution 22 is fed to the scrubber column MPSC. The LPR condensate solution stream 24 promotes the condensation of the vapours 6 while the LPR condensate solution stream 25 helps scrubbing the carbon dioxide from the carbamate solution 7 in the column MPSC.

It can be appreciated that, thanks to the invention, the ammonia and carbon dioxide contained in the vapours 19, released at a very low pressure (typically at atmospheric or near-atmospheric pressure), are conveniently recycled after condensation to the medium-pressure section MPR, namely to the condenser MPC and to the scrubber column MPSC. Accordingly, more ammonia is recycled to the column MPSC compared to the prior art, allowing for a proper feed of the nitric acid section NA by means of the ammonia gas 142 withdrawn from top of said column and a proper feed for the ammonium nitrate AN by means of the stream 11.

The vapours 26 from the atmospheric condenser AC are sent to the atmospheric scrubber AS together with vapours 27 withdrawn from the low-pressure condenser LPC. In the scrubber AS, said vapours 26 and 27 are scrubbed with the aid of make-up water 28 and the so obtained condensate 29 containing NH3, CO2 and water is recycled to the atmospheric condenser AC.

The injection of make-up water 28 is minimized by the ammonia recovery in the low-pressure condenser LPC, at intermediate pressure between the pressure of the recovery sections MPR and AR. A good portion of the ammonia is recovered at said low-pressure in the stream 18 and thus the offgas 19 contains a small amount of ammonia which can be easily condensed and scrubbed in the atmospheric condenser AC and scrubber AS using a reduced amount of make-up water 28.

Accordingly, the invention also allows to minimize the water injections in the system and finally to control the water content in the UAN product 33 which is generally restricted by applicable commercial specification.

The nitric acid section NA receives the ammonia feed 142 and an air feed 30. Fresh water 35 is also added in order to produce the nitric acid aqueous solution. The concentration of nitric acid in the solution 31 delivered by said section NA is typically 55 wt % to 65 wt % being water the balance to 100%.

Said solution 31 of nitric acid and the pressurized offgas 11 from the carbamate decomposer CD feed the section AN for production of ammonium nitrate. Said section AN produces ammonium nitrate aqueous solution 32 typically containing 75-95% of ammonium nitrate. The water excess is displaced as pure water 34.

Ammonium nitrate product 32 and the aqueous urea solution 15 withdrawn from the atmospheric decomposer AD feed the section UAN for the production of urea-ammonium nitrate 33.

Preferably the urea-ammonium nitrate 33 contains 44% of ammonium nitrate, 35% urea and balance water, resulting in a content of 32% of Nitrogen.

The streams 40 and 41 denote vented gas (e.g. inert gas) from sections NA and AN.

According to a variant (not shown) of the embodiment of FIG. 1, part of the ammonia 2 can feed the nitric acid section NA and/or the ammonium nitrate section AN.

In some embodiments the process is further integrated with the production of melamine. For example, referring to FIG. 1, a portion of the urea solution 15 is used to make melamine in a suitable melamine section; offgas extracted from the melamine section, and containing ammonia and carbon dioxide, can be reintroduced e.g. into the medium-pressure condenser MPC.

FIGS. 2 to 6 illustrates some variant embodiments. For the sake of simplicity, the items corresponding to FIG. 1 are denoted by the same numerals.

Figure 2:
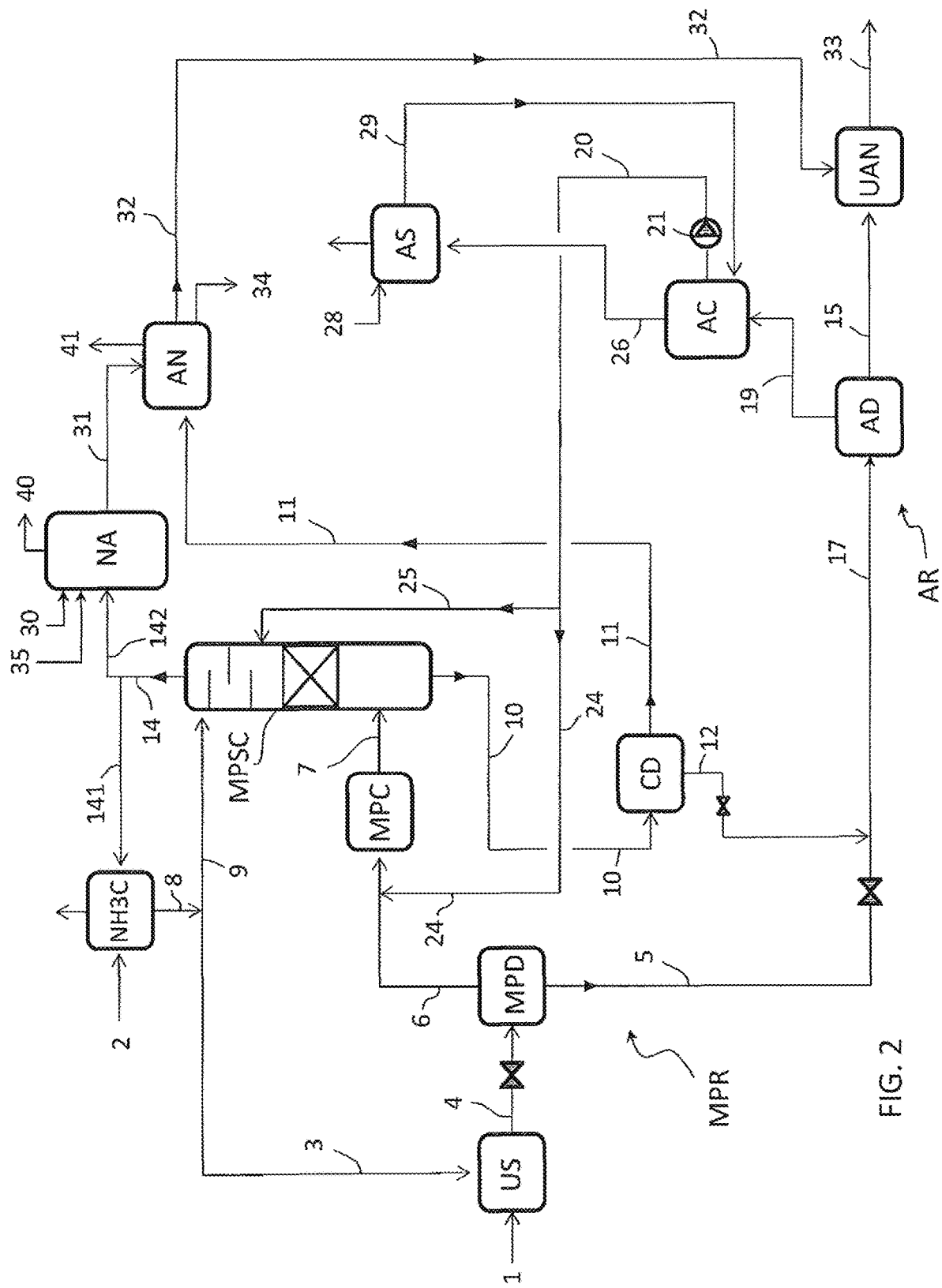
FIG. 2 illustrates an embodiment which is a variant of FIG. 1.

FIG. 2 illustrates an embodiment wherein the urea synthesis process includes only two recovery stages MPR and AR.

The stream 20 of condensate offgas, withdrawn from the atmospheric condenser AC, is fed directly to the medium-pressure recovery stage MPR. The stream 20 can be sent to one or more locations in the stage MPR. In the exemplary embodiment of FIG. 2, the stream 20 is split into portions 24 and 25, wherein the first portion 24 is fed to the medium-pressure condenser MPC and the second portion 25 is fed as a scrubbing medium to the column MPSC.

Figure 3:
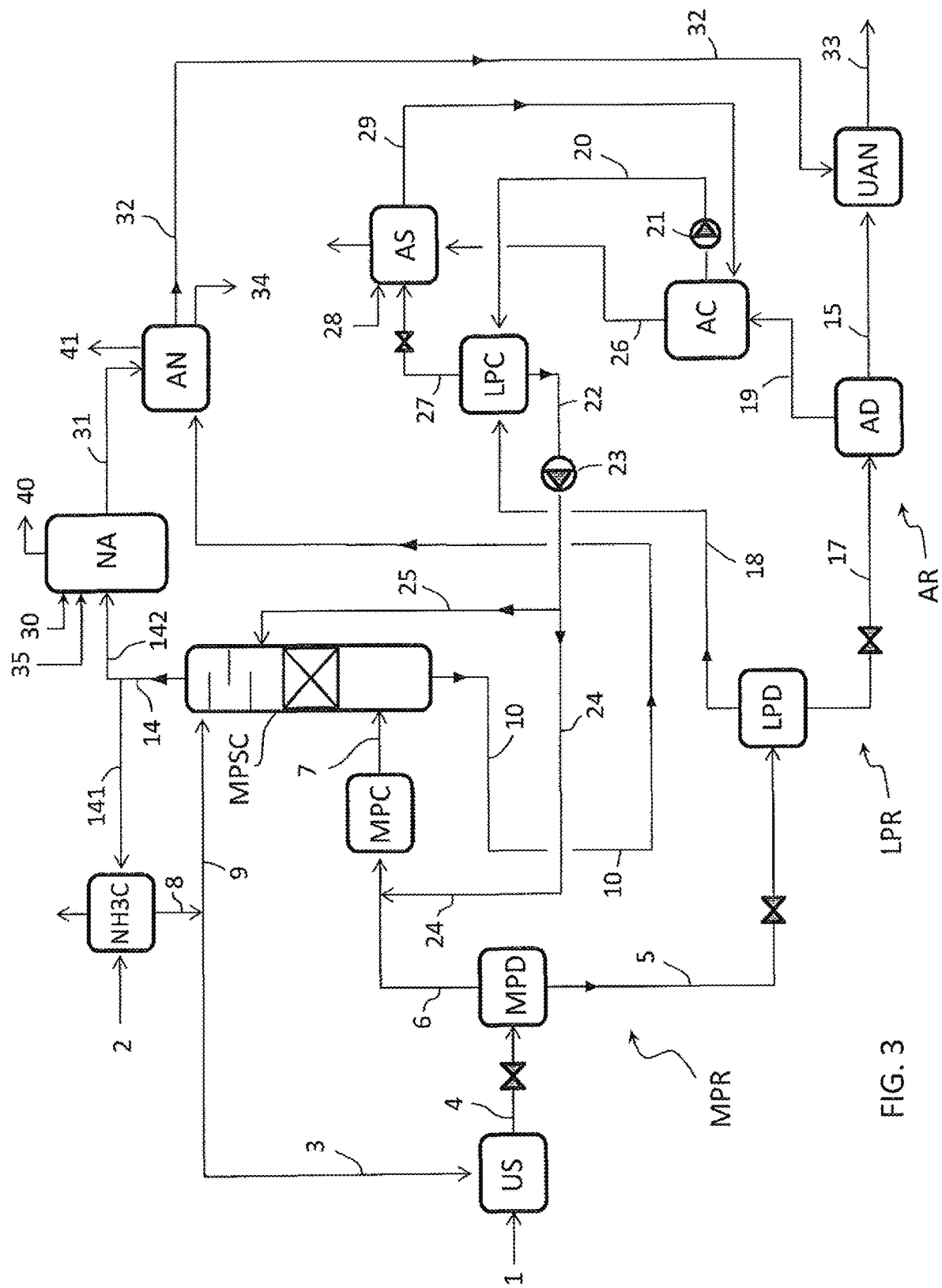
FIG. 3 illustrates an embodiment which is a further variant of FIG. 1.

FIG. 3 illustrates an embodiment wherein the carbamate solution 10 withdrawn from the bottom of the scrubber column MPSC is sent directly to the ammonium nitrate stage AN in the liquid state without the preliminary passage in the carbamate decomposer CD.

The embodiments of FIGS. 2 and 3 can be combined resulting in a further embodiment where the stream 20 goes directly to the section MPR and the solution 10 goes to the stage AN.

Figure 4:
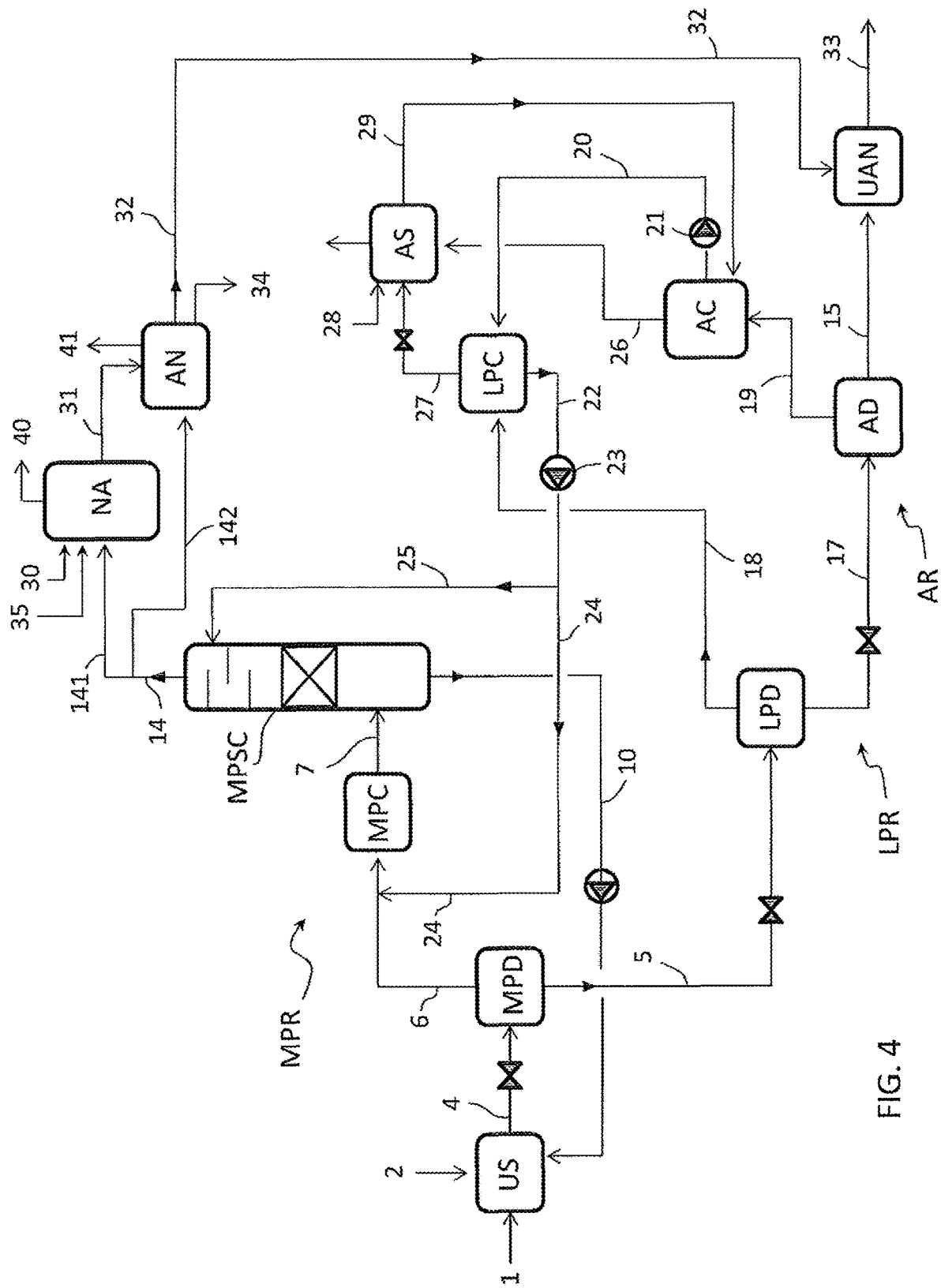
FIG. 4 illustrates an embodiment of the invention wherein urea is produced with a total-recycle process.

FIG. 4 illustrates an embodiment where the urea synthesis section US operates with a total-recycle process and the ammonia condenser NH3C is not necessary.

Ammonia 2 is fed directly to the urea synthesis section US. The medium scrubber column MPSC is fed only with condensate offgas stream 25 from the low pressure condenser LPC. A minor portion of the ammonia 2 can also feed the column MPSC in some embodiments.

The carbamate solution 10 from the column MPSC is recycled directly to the urea synthesis section US.

In a preferred embodiment the total ammonia 2 to produce the UAN product 33 is fed to the urea synthesis US and this allow to achieve optimum composition of the reagents into the synthesis reactor.

The ammonia gas 14 withdrawn from the columns MPSC is split into a first stream 141 and a second stream 142. The first stream 141 feeds the nitric acid section NA and the second stream 142 feeds the ammonium nitrate section AN.

Figure 5:
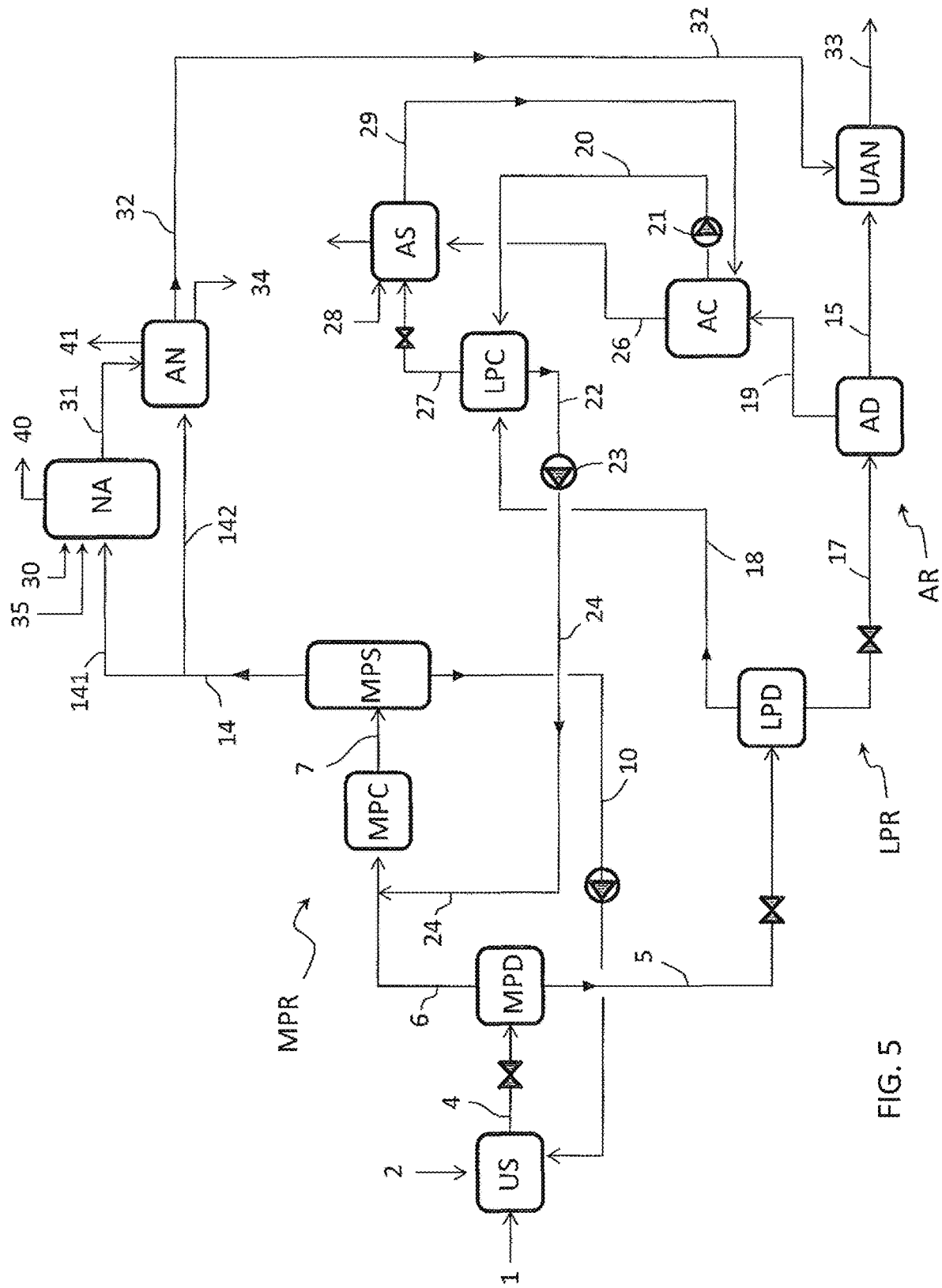
FIG. 5 illustrates a variant of FIG. 4.

FIG. 5 illustrates an embodiment wherein the scrubber column MPSC is replaced by a liquid gas separator MPS.

In this last case all the condensate offgas stream from the pump 23 is fed in the upstream side of the medium pressure condenser MPC, as stream 24.

Figure 6:
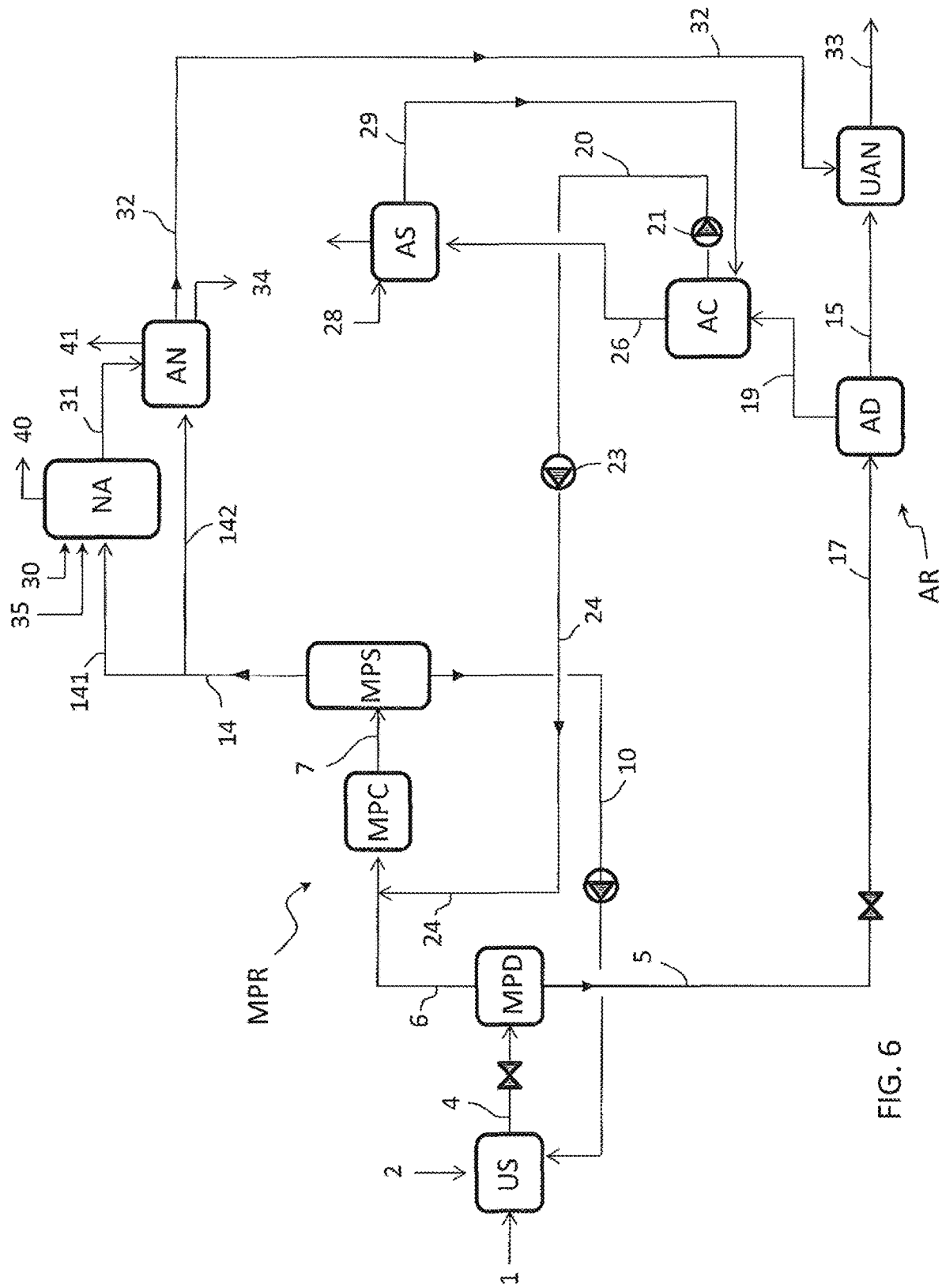
FIG. 6 illustrates a further embodiment.

FIG. 6 is a variant of FIG. 5 wherein the stream 20 containing the condensate offgas 19 is sent directly to the medium-pressure stage MPR, similar to FIG. 2.

The embodiment of FIG. 6 may include a medium-pressure separator MPS (as shown) or the scrubber column MPSC as in FIG. 4.

Figure 7:
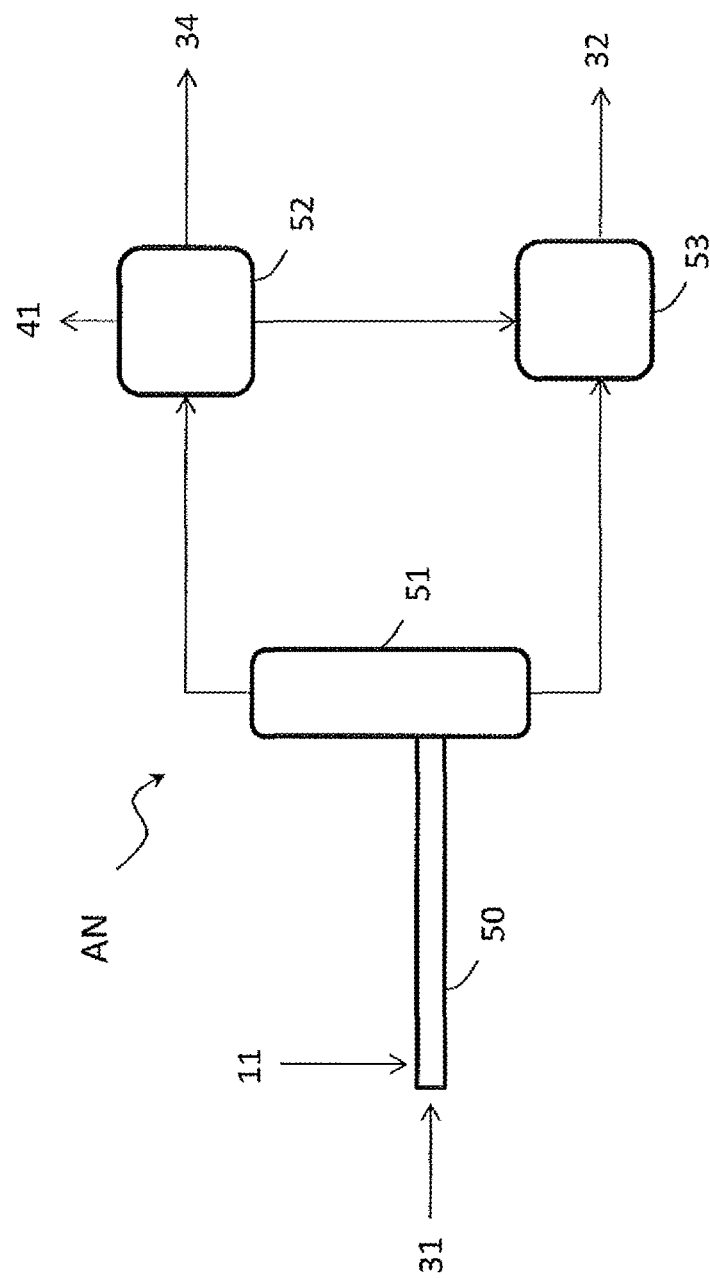
FIG. 7 illustrates a preferred embodiment of a nitric acid section including a pipe reactor.

FIG. 7 shows a preferred embodiment of the ammonium nitrate section AN comprising a pipe reactor 50, e.g. a reactor in the form of a vertical or more preferably horizontal pipe.

More in detail FIG. 7 shows an embodiment wherein the section AN includes a pipe reactor 50, a gas-liquid separator 51, a scrubber system 52 and a tank 53.

The offgas stream 11 (or 142 in the embodiment of FIG. 4) at pressure of 8-20 bar is fed to the pipe reactor 50. The nitric acid solution 31 is also fed to said pipe reactor. The medium pressure of the offgas stream 11 provides the mixing energy to promote the mixing between ammonia and nitric acid. At the outlet of the pipe reactor the ammonium nitrate (product of reaction) is separated as concentrated solution in the gas-liquid separator 51 working preferably at atmospheric pressure or close to the atmospheric.

The heat released by the reaction is removed by the vaporization of water contained into the streams 11 and 31 which is finally separated from the concentrated solution into the separator 51.

The vapours containing some entrained droplets of ammonium nitrate are treated in the scrubbing system 52 which discharges the inert gases 41 to the atmosphere (i.e. traces of nitrogen and inert gases coming with the offgas 11) and purified water 34 which can be safely disposed.

The solution from the separator 51 and a liquid phase withdrawn from the scrubbing system 52 are stored in the tank 53 and provides the solution 32 which is sent to the section UAN (FIGS. 1-6).

In some embodiments, the process of the invention can be further integrated with the production of ammonia, e.g. from reforming of a hydrocarbon.

Ammonia produced by a suitable ammonia synthesis section can feed the nitric acid stage NA or conveniently also to the AN section. In some embodiments the nitric acid section NA is fed with ammonia produced by the ammonia section and, consequently, the section NA is decoupled from the production of urea.

According to another variant of the invention, the pressurized offgas 11 are condensed and sent to the ammonium nitrate section AN in a liquid state, or the solution 10 is fed directly to the section AN without the step of decomposition in the decomposer CD.

The invention can also be applied to the revamping of existing integrated plants.

A common layout of a prior-art plant uses an atmospheric neutralizer in the section AN. Furthermore, a prior art plant may include the sections MPR and AR but does not include the section LPR and does not include the condenser AC. Then, the offgas emerging from the section AR are recycled in a gaseous form, typically to said atmospheric neutralizer.

A revamping to implement the above mentioned scheme may comprise for example:

adding the LPR section, working at a pressure intermediate between the working pressures of the existing sections MPR and AR;

adding the atmospheric condenser AC;

replacing the atmospheric neutralizer of the section AN with a neutralizer operating under pressure, preferably a pipe reactor, providing the necessary lines and pumps, compressors, etc.

By adding the atmospheric condenser AC and the LPR section, the offgas emerging from the section AR can be efficiently recycled to the higher-pressure section MPR as explained above.

The MPR section receives the condensate offgas from the second recovery stage thus receiving more ammonia and carbon dioxide and, therefore, is able to provide the pressurized offgas 11 for the ammonium nitrate section AN. Having a pressurized feed, the atmospheric neutralizer can be replaced with a safer and more efficient pressurized pipe reactor. Also, the MPR section is able to provide the ammonia gas 16 to feed the nitric acid section NA.

What is claimed is:

1. An integrated process for the production of urea and urea-ammonium nitrate, comprising:
   a) the production of aqueous solution of urea starting from ammonia and carbon dioxide, in a urea synthesis process;
   b) the production of ammonium nitrate from ammonia and nitric acid in a ammonium nitrate stage (AN),
   c) wherein at least part of said aqueous solution of urea is mixed with at least part of the ammonium nitrate to produce urea-ammonium nitrate in a urea-ammonium nitrate stage (UAN),
   d) said urea synthesis process comprising the reaction of ammonia and carbon dioxide at a synthesis pressure to form a urea reaction mixture containing urea and unconverted materials, and also comprising the recovery of unconverted materials in a plurality of recovery stages including at least a first recovery stage (MPR) operating at a first recovery pressure lower than said synthesis pressure, and a second recovery stage (AR) operating at a second recovery pressure lower than said first recovery pressure,
   the process being characterized by the following:
   e) offgas released by a step of carbamate decomposition (AD) in the second recovery stage, and containing unconverted ammonia, are at least partially condensed at said second recovery pressure, obtaining condensate offgas;
   f) recycling at least part of said condensate offgas, or a solution containing at least part of said condensate offgas, to said first recovery stage (MPR);
   g) withdrawing an ammonia-containing stream from said first recovery stage (MPR) at said first recovery pressure, and feeding said ammonia-containing stream to the ammonium nitrate stage (AN).

2. The process according to claim 1, the process being further integrated with a nitric acid stage (NA) for the production of a solution of nitric acid, wherein at least a portion of said solution of nitric acid is used for the production of ammonium nitrate in said ammonium nitrate stage (AN), the process comprising the step of:
withdrawing a substantially pure ammonia gas from said first recovery stage (MPR), and
feeding said ammonia gas to said nitric acid stage (NA).

3. The process according to claim 1, wherein said ammonia-containing stream withdrawn from the first recovery stage, either in a gaseous state or in a liquid state, is contacted with a solution of nitric acid in a pressurized pipe reactor of the ammonium nitrate stage.

4. The process according to claim 3, wherein said pressurized pipe reactor operates at a pressure substantially equal to said first recovery pressure.

5. The process according to claim 1, wherein said step f) includes feeding at least part of said condensate offgas directly to said first recovery stage (MPR).

6. The process according to claim 1, wherein:
the urea synthesis process comprises a third recovery stage (LPR) operating at a third recovery pressure which is lower than said first recovery pressure and greater than said second recovery pressure,
said third recovery stage (LPR) comprises a decomposition (LPD) of a urea solution obtaining a gas phase containing ammonia and carbon dioxide, and subsequent condensation (LPC) of said gas phase,
and said step f) includes:
mixing said condensate offgas with said gas phase before or during said condensation, obtaining a carbamate solution at said third pressure, and
recycling said carbamate solution to said first recovery stage (MPR).

7. The process according to claim 1, wherein said first recovery stage (MPR) comprises scrubbing carbon dioxide and ammonia vapours contained in a carbamate mixture after partial condensation in a condenser (MPC) of said with first recovery stage (MPR) obtaining a carbamate solution,
and wherein said ammonia-containing stream directed to the ammonium nitrate stage includes said carbamate solution obtained after scrubbing or vapours obtained from a subsequent step of decomposition of said diluted carbamate solution.

8. The process according to claim 7, wherein said first recovery stage (MPR) comprises the steps of:
decomposition of the urea reaction mixture, obtaining a urea solution and a gas phase containing ammonia and carbon dioxide;
partial condensation of said gas phase obtaining the carbamate solution and carbon dioxide and ammonia vapors which is subjected to said scrubbing.

9. The process according to claim 8, wherein said step f) includes:
recycling a first portion of said solution containing condensate offgas to said step of partial condensation of the gas phase obtained after decomposition of the reaction mixture, said first portion of solution being mixed with said gas phase before or during condensation;
recycling a second portion of said solution to said scrubbing process, for use as a scrubbing medium.

10. The process according to claim 7, wherein the process is further integrated with a nitric acid stage (NA) for the production of a solution of nitric acid, the process further comprising the step of: withdrawing a substantially pure ammonia gas from said scrubbing process and feeding said ammonia gas to said nitric acid stage.

11. The process according to claim wherein:
said first recovery pressure is in the range of 2 to 25 bar, and/or
said second recovery pressure is atmospheric or is a near-atmospheric pressure slightly above the atmospheric pressure, and/or
said third recovery pressure is in the range of 2 to 6 bar.

12. The process according to claim 1, said ammonia-containing stream from the first recovery stage having a purity of at least 90 wt %.

13. The process according to claim 1, wherein urea is produced with any of: a total-recycle process, a partial-recycle process, a once-through process.

14. A urea-UAN integrated plant for carrying above a process according to claim 1, said plant comprising:
a urea synthesis section (US) for the production of aqueous solution of urea starting from ammonia and carbon dioxide;
a urea-ammonium nitrate section (UAN) wherein at least part of said aqueous solution of urea is mixed with ammonium nitrate to produce urea-ammonium nitrate;
said urea synthesis section (US) comprising a synthesis loop for the reaction of ammonia and carbon dioxide at a synthesis pressure to form a reaction mixture containing urea and unconverted materials, and also comprising a plurality of recovery sections including at least a first recovery section (MPR) operating at a first recovery pressure lower than said synthesis pressure, and a second recovery section (AR) operating at a second recovery pressure lower than said first recovery pressure,
wherein:
said second recovery section (AR) comprises a carbamate decomposer (AD) and a condenser (AC) for a partial condensation of offgas released by said carbamate decomposer (AD), obtaining condensate offgas;
the plant comprises at least one line arranged to recycle at least part of said condensate offgas, or a solution containing at least part of said condensate offgas, to said first recovery section (MPR);
the plant also comprises at least one line to feed an ammonia-containing stream from said first recovery stage (MPR) to the ammonium nitrate stage (AN).

15. A method for modifying a urea-UAN integrated plant, wherein:
said integrated plant comprises a urea section for production of an aqueous solution of urea, an ammonium nitrate section for production of ammonium nitrate and a urea-ammonium nitrate section for production of UAN from said solution of urea and ammonium nitrate,
said urea section includes at least a first recovery section (MPR) working at a first pressure and a second recovery section (AR) operating at a second pressure lower than said first pressure,
said method comprising:
the installation of an additional condenser (AC) in said second recovery section, for condensing a current of offgas released by a carbamate decomposer of said second recovery section, obtaining condensed offgas;
the provision of a line to recycle a solution containing said condensate offgas to said first recovery stage (MPR);
the provision of a line to withdraw a pressurized ammonia-containing stream from said first recovery section (MPR) and recycling said pressurized ammonia-containing stream to the ammonium nitrate section.

16. The method according to claim 15, further comprising:
    installation of an additional low-pressure recovery section (LPR) in the urea section, said additional recovery section operating at a third pressure lower than said first pressure but greater than said second pressure,
    said additional low-pressure recovery section comprising at least a decomposer and a low-pressure condenser for condensation of gas containing ammonia and carbon dioxide,
    sending said solution containing condensate off gas to the low-pressure condenser of said low-pressure recovery section,
    feeding a recycle solution containing ammonia and obtained from said low-pressure condenser to said medium-pressure recovery section.

17. A method according to claim 15, wherein said ammonium nitrate section originally comprises an atmospheric neutralizer, the method comprising the replacement of said neutralizer with a pipe reactor, said pipe reactor being fed with said pressurized ammonia-containing stream withdrawn from the medium-pressure recovery section.

18. The process according to claim 11, wherein:
    said first recovery pressure is in the range of 5 to 20 bar, and/or
    said second recovery pressure is atmospheric or is not greater than 1 barg, and/or
    said third recovery pressure is about 3 bar.

19. The process according to claim 11, wherein:
    said first recovery pressure is in the range of 8 to 20 bar, and/or
    said second recovery pressure is atmospheric or is about 0.5 barg, and/or
    said third recovery pressure is about 3 bar.

* * * * *